United States Patent
Woods et al.

(10) Patent No.: US 6,916,890 B1
(45) Date of Patent: Jul. 12, 2005

(54) THERMALLY REWORKABLE EPOXY RESINS AND COMPOSITIONS BASED THEREON

(75) Inventors: John G. Woods, Farmington, CT (US); Susanne D. Morrill, West Hartford, CT (US)

(73) Assignee: Henkel Corporation, Rocky Hill, CT (US)

( * ) Notice: Subject to any disclaimer, the term of this patent is extended or adjusted under 35 U.S.C. 154(b) by 526 days.

(21) Appl. No.: 10/201,977

(22) Filed: Jul. 25, 2002

Related U.S. Application Data
(60) Provisional application No. 60/328,055, filed on Oct. 9, 2001.

(51) Int. Cl.[7] .................. C07C 67/05; C07C 69/73; C07D 301/12; C07D 303/20; C08L 63/00
(52) U.S. Cl. .................. 525/524; 427/386; 438/127; 525/481; 525/485; 525/486; 525/526; 525/528; 549/523; 549/546; 560/55; 560/60; 560/64; 560/128; 560/183
(58) Field of Search .................. 525/481, 524, 525/526, 527, 485, 486; 549/523, 546, 549; 560/55, 60, 64, 128, 183; 427/386; 438/127

(56) References Cited

U.S. PATENT DOCUMENTS

| | | | | |
|---|---|---|---|---|
| 3,856,728 A | * | 12/1974 | Abramoff | 524/114 |
| 5,319,024 A | | 6/1994 | Ishidoya et al. | 525/123 |
| 5,352,740 A | | 10/1994 | Ishidoya et al. | 525/119 |
| 5,419,929 A | | 5/1995 | Ishidoya et al. | 427/386 |
| 5,512,613 A | | 4/1996 | Afzali-Ardakani et al. | 523/443 |
| 5,516,839 A | | 5/1996 | Ishidoya et al. | 525/34 |
| 5,549,932 A | | 8/1996 | Ishidoya et al. | 427/385.5 |
| 5,560,934 A | | 10/1996 | Afzali-Ardakani et al. | 424/497 |
| 5,783,867 A | | 7/1998 | Belke et al. | 257/783 |
| 5,973,033 A | | 10/1999 | Ober et al. | 523/443 |
| 6,323,360 B1 | * | 11/2001 | Ruckenstein et al. | 560/199 |
| 6,667,194 B1 | * | 12/2003 | Crane et al. | 438/127 |

FOREIGN PATENT DOCUMENTS

| | | | | |
|---|---|---|---|---|
| EP | 548603 | 6/1993 | | 21/60 |
| JP | 06-69280 | 3/1994 | | 21/60 |
| JP | 06-77254 | 6/1994 | | 21/52 |
| WO | 98/31738 | 7/1998 | | 5/9 |

OTHER PUBLICATIONS

CAPLUS accession No. 1988:204195, Nedolya et al., "(Vinyloxy)alkyl acylals of acetaldehyde. Vinyloxy acrylate analogs," Zhurnal Organicheskoi khimii, vol. 23, No. 6, 1987, abstract.*

S Yang. J Chen H Korner T Breiner and C Ober Reworkable Epoxies Thermosets with Thermally Cleavable Groups for Controlled Network Breakdown *JACS* vol 10, No 6 (Jun. 1998).

K Ogino. J Chen and C Ober "Synthesis and Characterization of Thermally Degradable Polymer Networks" *JACS* vol 10 No 12, Mar. 1998.

* cited by examiner

*Primary Examiner*—Robert Sellers
(74) *Attorney, Agent, or Firm*—Steven C. Bauman (57) ABSTRACT

The present invention discloses reworkable epoxy compositions suitable for encapsulation of and underfill for electronic components including (a) the epoxidized reaction product of a multifunctional 1-alkenyl ether or 1-cycloalkenyl ether and an alkenyl carboxylic acid, the epoxidized reaction product having two or more thermally labile alpha-alkoxy ester linkages; and (b) a curing agent for the epoxy component. The epoxy composition, when cured, provides a composition which is thermally reworkable, the weak α-alkoxy ester linkages providing for the reworkable aspect of the invention.

8 Claims, 2 Drawing Sheets

THERMALLY REWORKABLE EPOXY RESINS AND COMPOSITIONS BASED THEREON

This application claims the benefit of Provisional application No. 60/328,055 filed on Oct. 9, 2001.

FIELD OF THE INVENTION

This invention relates generally to thermosetting resin compositions which are useful for encapsulation of and underfill for electronic components, where easy removal of the components for repair or replacement is required. In particular, this invention relates to reworkable epoxy resins used for mounting onto a circuit board semiconductor devices, such as chip size or chip scale packages ("CSPs"), ball grid arrays ("BGAs"), land grid arrays ("LGAs"), and the like, each of which have a semiconductor chip, such as large scale integration ("LSI"), on a carrier substrate.

BRIEF DESCRIPTION OF RELATED TECHNOLOGY

In recent years, the popularity of small-sized electronic appliances, such as camera-integrated video tape recorders ("VTRs") and portable telephone sets, has made size reduction of LSI devices desirable. As a result, CSPs, BGAs, and LGAs are being used to reduce the size of packages substantially to that of bare chips. Such CSPs, BGAs, and LGAs improve the characteristics of the electronic device while retaining many of their operating features, thus serving to protect semiconductor bare chips, such as LSIs, and facilitate testing thereof.

Ordinarily, the CSP/BGA/LGA assembly is connected to electrical conductors on a circuit board by use of a solder connection or the like. However, when the resulting CSP/BGA/LGA circuit board structure is exposed to thermal cycling, the reliability of the solder connection between the circuit board and the CSP/BGA/LGA often becomes suspect. Recently, after a CSP/BGA/LGA assembly is mounted on a circuit board, the space between the assembly and the circuit board is often now filled with a sealing resin (often referred to as underfill sealing) in order to relieve stresses caused by thermal cycling, thereby improving heat shock properties and enhancing the reliability of the structure.

However, since thermosetting resins are typically used as the underfill sealing material, in the event of a failure after the CSP/BGA/LGA assembly is mounted on the circuit board, it is very difficult to replace the assembly without destroying or scrapping the structure in its entirety. Therefore, there has been an ongoing search for resins that will allow easy removal of packaged chip components for recycling, repair or replacement. The cured resins which are being sought are referred to as reworkable in the art.

To that end, techniques for mounting a bare chip on a circuit board are accepted as substantially similar to the mounting of a CSP/BGA/LGA assembly onto a circuit board. Japanese Laid-Open Patent Publication No. 69280/94 discloses a process where a bare chip is fixed and connected to a substrate by use of a resin capable of hardening at a predetermined temperature. In the event of failure, this bare chip is removed from the substrate by softening the resin at a temperature higher than the predetermined temperature. However, no specific resin is disclosed, and there is no disclosure about treating the resin which remains on the substrate.

As pointed out in Japanese Laid-Open Patent Publication No. 77264/94, it is conventional to use a solvent to remove residual resin from a circuit board. However, swelling the resin with a solvent is a time consuming process and the corrosive organic acid ordinarily used as the solvent may reduce the reliability of the circuit board. Instead, that disclosure speaks to a method for removing residual resin by irradiation with electromagnetic radiation.

Japanese Laid-Open Patent Publication No. 251516/93 also discloses a mounting process using a commercially available bisphenol A type epoxy resin (CV5183 or CV5183S; manufactured by Matsushita Electric Industrial Co., Ltd.). However, the removal process so disclosed does not consistently permit easy removal of the chip, the curing step is lengthy at elevated temperatures, and the process generally results in poor productivity.

Thermoplastic underfill resins are known for use in semiconductor chip attachment. See U.S. Pat. No. 5,783,867 (Belke, Jr.). However, such thermoplastic resins tend to leak under relatively modest temperature conditions. In contrast, thermosetting resins cure into a matrix which ordinarily have greater thermal stability under end-use operating temperatures.

Several classes of labile-group functionalized diepoxide monomers have been examined as reactive components of reworkable underfill adhesives for the bonding and reinforcement of solder-bumped flip-chip attachments to circuit boards. Such adhesives contain, in addition to the epoxide monomer(s) suitable curing agents and/or catalysts including anhydrides, amines and thiols. On heating, these compositions cure to form network structures that exhibit sufficient adhesive strength to mechanically stabilize the soldered devices. In addition, they are characterized by having a thermally labile or readily hydrolyzable function that permits the network to be readily degraded when the device is heated at elevated temperatures and/or when it is exposed to an acidic solution. The labile groups that have been used to impart reworkable properties to the epoxy adhesive include secondary and tertiary esters, aliphatic acetals and various carbamates.

For example, U.S. Pat. No. 5,512,613 (Afzali-Ardakani) and U.S. Pat. No. 5,560,934 (Afzali-Ardakani), each refer to a reworkable thermoset composition formed from (a) a diepoxide component in which the organic linking moiety connecting the two epoxy groups of the diepoxide includes an acid cleavable acyclic acetal group; (b) an anhydride curing agent; (c) a 1,3-diaza compound and (d) a hydroxy functional initiator. The acid cleavable acyclic acetal group forms the basis of the reworkable composition. The use of acidic solutions to decompose the cured product may compromise the integrity of electrical devices and adds considerable inconvenience and cost to the decompositon process. Moreover, the disclosed composition does not allow for reworkability via thermal decomposition; the decomposition of conventional epoxy-based thermoset adhesives generally occurs at temperatures in excess of 300° C. and these materials would therefore be unsuitabe for use in thermally reworkable applications where rapid degradation at temperatures exceeding 200° C., desirably, 220–280° C. are required.

International Patent Publication No. PCT/US98/00858 refers to a thermosetting resin composition capable of sealing underfilling between a semiconductor device including a semiconductor chip mounted on a carrier substrate and a circuit board to which said semiconductor device is electrically connected. The composition includes about 100 parts by weight of an epoxy resin, about 3 to about 60 parts by weight of a curing agent, and about 1 to about 90 parts by weight of a plasticizer. Here, the area around the cured thermoset is to be heated at a temperature of about 190 to about 260° C. for a period of time ranging from about 10 seconds to about 1 minute in order to achieve softening and a loss of much of its adhesiveness.

U.S. Pat. No. 5,549,932 (Ishidoya) discloses the production of blocked carboxylic acids for use as one-part thermosetting compositions which are formed by the reaction of polycarboxylic acids with vinyl ethers in the presence of acid catalysts, as described in column 5, lines 26–48 and column 7, lines 40–44 of the specification. One reaction product disclosed is a compound having in the molecule two or more carboxyl groups blocked by a vinyl ether group and two or more reactive epoxy groups which may be in the same molecule as the blocked carboxy groups. These products contain an epoxy acetal group as part of a weak α-alkoxy ester linkage used for generating an epoxy curing agent, wherein an α-alkoxy ester is defined here as having an alkoxy group which is alpha to the ethereal oxygen atom of the ester group. For example, these products are initially heated to deblock the polycarboxylic acid via the destruction of the thermally-labile ester linkage. The acid then functions as a curing agent of suitably reactive resins including epoxides, as described in column 7, lines 48–57, in which a polymerization or network forming reaction occurs to give the cured polymeric materials having good chemical and physical properties. Such materials are, however, not suitable for reworkable adhesives due to their lack of a thermally-labile linkage in the cured product, the labile linkage having been destroyed in the heating step used to generate the curing agent. Moreover, the acid catalysts used for the reaction of the polycarboxylic acid with an epoxidized vinyl ether can reduce the storage stability of the epoxide monomer and reduce the degradation temperature of the cured adhesive to a temperature below that which is useful for maintenance of its intended application, such as for an underfill for electronic components where stability during thermal cycling is required.

U.S. Pat. No. 5,973,033 (Ober) discloses compounds providing reworkable cured thermosets which contain two cyclic hydrocarbon moieties which are substituted, for example, with an epoxy group to provide crosslinking functionality, and which are linked to each other by a secondary or tertiary oxycarbonyl-containing moiety for formation of an epoxidized secondary or tertiary ester which, when cured provides a composition which decomposes at moderate temperatures.

Despite the state-of-the-technology, it would be desirable for an underfilling sealing material to provide good productivity and thermal shock properties, while allowing the substrates, e.g. circuit boards, with which it is to be used to be readily processed and easily separated from a semiconductor device, without application of strongly acidic media or elevated temperature conditions that may compromise the integrity of the semiconductor devices remaining on the substrate or the substrate itself. It would farther be desirable to provide an easy and cost-effective method for synthesizing an epoxy resin compound , which when cured provides a reworkable thermosetting composition, the method for which would ideally employ raw materials which are commercially available and which could be performed without acid catalysts. It would also be beneficial to provide a means for lowering the decomposition temperature of cured formulations of commercially available epoxide monomers by providing an additive for thermosetting resin compositions which is substantially free of unreacted acid or acidic impurities. Such acid impurites can impede the curing process and reduce the storage stability of the epoxide monomor.

SUMMARY OF THE INVENTION

The present invention satisfies a need by providing reworkable epoxy adhesives that decompose rapidly at relatively high temperatures, are inexpensive to produce, do not generate toxic by-products on decomposition and leave residues that are easy to clean.

The present invention provides a thermosetting epoxy resin composition, which when cured provides a composition which is thermally reworkable and is suitable for encapsulation of or underfill for electronic components. The invention includes the epoxidized reaction product of multifunctional 1-alkenyl or 1-cycloalkenyl ether and an alkenyl carboxylic acid, the epoxidized reaction product having two or more thermally labile alpha-alkoxy ester linkages and a curing agent. The reaction products form a thermally reworkable networked polymer in the presence of the curing agent. Desirably, the alkenyl carboxylic acid is mono-alkenyl carboxylic acid.

Reaction products of these compositions are capable of softening under exposure to elevated temperature conditions, such in excess of the temperatures used to cure the composition. Such temperature exposure combined with the epoxy compound having two or more thermally cleavable linkages (i.e. alpha-alkoxy ester linkages) provides the reworkable aspect of this invention. The α-alkoxy esters linking the two epoxide functional groups are quantitatively broken by heating at moderately high temperatures. An additional reworkable aspect is achieved by exposing the reaction products of these compositions to dilute acid.

In another aspect of the invention there is provided curable epoxy resin compounds which may be represented by one of the following formulae:

Formula (a)

Formula (b)

wherein G denotes an organic group derived from a multifunctional 1-alkenyl ether; R represents a $C_1$–$C_6$ alkyl group; E represents an organic group fragment derived from a mono-alkenyl carboxylic acid that has been epoxidized at the alkenyl group; n represents an integer from 2–30, desirably, an integer from 2–6; Y denotes an organic group fragment derived from a multifunctional 1-cycloalkenyl ether in which the cyclic ether groups are linked through Y; and m represents the integer 1 or 2. In particular, G may be a hydrocarbon, ether, thioether, ester, thioester, carbamate, amide, or a combination of these groups; G may be a low molar mass entity or an oligomeric or polymeric species. Y in Formula (b) may be attached to the ring portion of the structure at any carbon position other than the carbon atom located between the two oxygen atoms of the acetal fragment or the carbon atom alpha to this position. More specifically, Y may be a hydrocarbon, ether, thioether, ester, thioester carbamate, amide or a combination of these groups; it may be a low molar mass entity or an oligomeric or polymeric species.

The present invention further provides a reworkable epoxy composition, which when cured provides a composition which is thermally degradable and is suitable for encapsulation of or underfill for electronic components. In one embodiment, the reworkable composition includes: (a) a curable epoxy component including the epoxidized reaction product of a multifunctional 1-alkenyl or 1-cycloalkenyl ether and an alkenyl carboxyl acid, the curable epoxy component being present in an amount within the range of about 20 to about 65 weight percent, based on the total weight of the composition; (b) an anhydride curing agent in an amount within the range of about 0.5 to about 1.3 equivalents of anhydride per equivalent of epoxide; (c) an inorganic filler component in an amount up to about 70 weight percent, based on the total weight of the composition; and (d) a flowability agent in an amount up to about 0.5 weight percent, based on the total weight of the composition. In another embodiment, the reworkable composition may contain a primary or secondary amine curing agent in an amount within the range of about 0.5 to about 2.0 equivalents of amine per equivalent of epoxide.

The inventive reworkable epoxy composition is particularly useful as an underfilling sealing resin, and enables a semi-conductor device, such as a CSP/BGA/LGA assembly which includes a semi-conductor chip mounted on a carrier substrate, to be securely connected to a circuit board by short-time heat curing and with good productivity. Reaction products of the inventive compositions demonstrate excellent heat shock properties, also referred to as thermal cycle properties, and permit the semiconductor device to be easily removed from the circuit board by localized heating or dilute acid in the event of semi-conductor device or connection failure. This makes it possible to reuse the circuit board (with the remaining functioning semiconductor devices still electrically attached) and thereby achieve an improvement in the yield of the production process and a reduction in production cost.

The compositions of this invention may also be used for micro-electronic applications beyond sealing underfill, such as with glob top, die attachment and other applications for thermosetting compositions in which rapid cure time and an extended useful working life are desirable.

The epoxy resin component of the composition of the present invention is also useful as an additive for lowering the degradation temperature of a cured formulation of a commercially available epoxy monomer. Such an epoxy additive provided by the present invention is a curable epoxy compound which is the epoxidized reaction product of a multifunctional 1-alkenyl or 1-cycloakenyl ether and an alkenyl carboxylic acid, the reaction product being substantially free of unreacted acid or acid impurities.

In yet another aspect of the invention, there is provided a method for synthesizing an epoxy monomer which includes the steps of (a) reacting a 1-alkenyl or 1-cycloalkenyl ether with an alkenyl carboxylic acid at a ratio of at least 1 equivalent of n-functional 1-alkenyl or 1-cycloalkenyl ether per n equivalents of alkenyl carboxylic acid, where n is an integer within the range of 1–6, to form an intermediate; and (b) epoxidizing the carbon-carbon double bonds of the intermediate in (a). These carbon-carbon double bonds in the intermediate are derived from the alkenyl carboxylic acid. Desirably, the alkenyl carboxylic acid is a mono-alkenyl carboxylic acid.

Further provided by the invention is the reaction product of a 1-alkenyl or 1-cycloalkenyl ether and an alkenyl carboxylic acid, the reaction product corresponding to the reaction intermediate formed in step (a) of the method for forming the epoxy monomer described above. The reaction intermediate may be represented by one of the following formulae:

Formula (c)

Formula (d)

wherein G denotes an organic group derived from a multifunctional 1-alkenyl ether; R represents a $C_1$–$C_6$ alkyl group; $R_8$ represents an organic group that contains an alkenyl group; n represents an integer from 2–30; Y denotes an organic group fragment derived from a multifunctional 1-cycloalkenyl ether in which the cyclic ether groups are linked through Y; and m represents the integer 1 or 2. Specific organic groups for G and Y are the same as those described above for Formulae (a) and (b).

In another aspect of the present invention, there is provided a method for synthesizing the multiolefinic alpha-alkoxy ester intermediate compound represented by one of Formulae (c) and (d) above. The method includes reacting a multifunctional 1-alkenyl or 1-cycloalkenyl ether with an alkenyl carboxylic acid at a ratio of at least 1 equivalent of n-functional 1-alkenyl or 1-cycloalkenyl ether per n equivalents of mono-alkenyl carboxylic acid, where n is an integer within the range of 1–6. Subsequent expoxidition of the carbon-carbon double bonds of the alkenyl group in $R_8$ of Formula (c) or Formula (d) with a peroxidic reagent forms the epoxy monomer of the present invention.

Suitable reagents for synthesis of the intermediate are described above.

The invention further provides for a method for preparing a thermosetting epoxy resin composition, which when cured provides a composition which is thermally reworkable and which is suitable for encapsulation of or underfill for electronic components. The inventive method includes combining in admixture: (a) a curable epoxy component including the epoxidized reaction product of a multifunctional 1-alkenyl or 1-cycloalkenyl ether and an alkenyl carboxylic acid; and (b) a curing agent component; and permitting the admixture to cure. Useful curing agents include nitrogen-containing agents, anhydrides, polyphenols, polyisocyanates, and thiol-containing agents. Nitrogen-containing curing agents for use with the present invention include amines, heterocyclic amines, functionalized amines, cyanate esters, or combinations thereof.

The present invention provides generally a way in which to lower the decomposition temperature of cured formulations of commercially available epoxide monomers is disclosed, wherein the method includes admixing: (a) a curable epoxy component including the epoxidized reaction product of a multifunctional 1-alkenyl or 1-cycloalkenyl ether and an alkenyl carboxylic acid; (b) a curing agent component, such as a nitrogen-containing compound or anhydride; and (c) a commercially available epoxy monomer, such as an epoxidized diglycidyl ether of a bisphenol. The curable epoxy component of the reworkable epoxy compositions provided by the present invention serve as the additive which lowers the degradation temperature of the cured formulation of the commercially epoxy resin monomer, thereby increasing the workability of commercially available monomers upon cure.

Other benefits and advantages of the present invention are discussed below.

DETAILED DESCRIPTION OF THE INVENTION

The decomposition of conventional epoxy-based thermoset adhesives generally occurs at temperatures in excess of 300° C. and these materials are, therefore, unsuitable for use in thermally reworkable applications. In thermally reworkable applications, it is required that the cured underfill adhesive be able to withstand solder reflow temperatures without significant decomposition, i.e. at temperatures up to about 200° C. At the same time, it is required that they undergo a rapid degradation at temperatures exceeding this value, particularly in the range of 220–280° C. Multi-functional epoxidized alkoxyalkyl ester monomers according to the present invention which have been cured with anhydride curing agents have thermal decomposition profiles that make them particularly suitable for reworkable underfill adhesives. In addition, the monomers are readily prepared in two-steps from commercially available and inexpensive raw materials and have been found to leave decomposition residues that are easy to clean. This report describes the synthesis, prototype adhesive formulation, and thermal analysis of multi-functional epoxidized alkoxyalkyl ester monomers and the cured polymers derived from these monomers.

The reworkable epoxy resin compositions provided by the present invention which are useful for encapsulation of and underfill for electronic components, include: a) a curable epoxy component, including the epoxidized reaction product of a multifunctional 1-alkenyl or 1-cycloalkenyl ether and an alkenyl carboxylic acid; and (b) a curing agent component for the epoxy component. Desirably, the alkenyl carboxylic acid is a mono-alkenyl carboxylic acid. A suitable curing agent for use in the inventive epoxy compositions is herein defined as a curing agent, a catalyst, or both a curing agent and a catalyst.

Epoxidation of the isolated reaction intermediate formed in step (a) yields the epoxy monomer of the present invention. The reaction products are desirably substantially free of unreacted acid or acid impurities. The reaction of the 1-alkenyl or 1-cycloalkenyl ether with the mono-alkenyl carboxylic acid can be performed in the absence of acid catalysts. Acid catalysts are undesirable as they tend to reduce the storage stability of the epoxide monomer and reduce the degradation temperature of the cured adhesive polymer. Step (a) employs raw materials which are commercially available.

Multi-functional 1-alkenyl ethers useful in the preparation of the compound of Formula (a) shown above may be represented by the following structure:

wherein $R_1$ is hydrogen or $C_1$–$C_5$ alkyl group and G and n are as already described.

Multi-functional 1-cycloalkenyl ether useful in the preparation of the compound of Formula (b) shown above may be represented by the following structure:

wherein Y, m and n are as already described.

Mono-alkenyl carboxylic acids useful in the production of the compounds represented by Formulae (a) and (b) are organic compounds containing one alkenyl group and one carboxylic acid group in the same molecule. Such compounds be represented by, but are not limited to, the following structures:

wherein $R_2$, $R_3$ and $R_4$ are independently selected from H, $C_1$–$C_{20}$ alkyl, cycloalkyl, aryl, alkaryl, and alkoxy; $R_5$, which may or may not be present, is $C_1$–$C_{20}$ alkyl, cycloalkyl, aryl, alkaryl, and alkoxy; $R_6$ and $R_7$ represent $C_1$–$C_6$ alkyl groups that may be further linked to produce bicyclic structures. "n" is an integer having a value between 1 and 8.

Suitable multifunctional 1-alkenyl ether compounds include the following: 1,6-hexanediol divinylether, 1,4-cyclohexane dimethanol divinyl ether, trimethylolpropane trivinylether, diethyleneglycol divinyl ether, polyoxyethylene divinyl ether, ethyleneglycol divinyl ether, tetraethyleneglycol divinyl ether, bis[4-(vinyloxy)butyl]isophthalate, bis[4-(vinyloxymethyl)cyclohexylmethyl]glutarate, bis[4-(vinyloxy)butyl]succinate, bis[4-(vinyloxy)butyl]adipate, bis[4-(vinyloxy)butyl](methylene di-4,1-phenylene) biscarbamate, tris[4-(vinyloxy)butyl]trimellitate, butanediol divinyl ether, nonandiol divinylether, cyclohexanediol divinylether, pentaerythritol-tetravinyl ether, 1,4-dipropenoxybutane, 1,6-dipropenoxyhexane, 1,6-dipropenoxyoctane, 1,10-dipropenoxydecane, diethyleneglycoldipropenyl ether, neopentylglycoldipropenyl ether, triethyleneglycoldipropenyl ether, trimethylolpropanetripropenyl ether, 1,2,3-tripropenoxypropane, pentaerythritoltetrapropenyl ether, and sorbitolhexapropenyl ether.

The mono-alkenyl carboxylic acid may be selected from the following: 3-cyclohexene-1-carboxylic acid, 2-hexenoic acid, 3- hexenoic acid, 4hexenoic acid, acrylic acid, methacrylic acid, crotonic acid, vinyl acetic acid, tiglic acid, 3,3-dimethylacrylic acid, trans-2-pentenoic acid, 4-pentenoic acid, trans-2-methyl-2-pentenoic acid, 2,2-dimethyl-4-pentenoic acid, trans-2-hexenoic acid, trans-3-hexenoic acid, 2-ethyl-2-hexenoic acid, 6-heptenoic acid, 2-octenoic acid, (+/−)-citronellic acid, (R)-(+)-citronellic acid, (S)-(−)-citronellic acid, undecylenic acid, myristoleic acid, palmitoleic acid, oleic acid, elaidic acid, cis-11-eicosenoic acid, erucic acid, nervonic acid, cis-3-chloroacrylic acid, trans-3-chloroacrylic acid, 2-bromoacrylic acid, 2-(trifluoromethyl)acrylic acid, 2-(bromomethyl)acrylic acid, 2-cyclopentene-1-acetic acid, (1R-trans)-2-(bromomethyl)-2-methyl-3-methylenecyclopentaneacetic acid, 2-acetamidoacrylic acid, 5-norbornene-2-carboxylic acid, 3-(phenylthio)acrylic acid, trans-styrylacetic acid, trans-cinnamic acid, alpha-methylcinnamic acid, alpha-phenylcinnamic acid, 2-(trifluoromethyl)cinnamic acid, 2-chlorocinnamic acid, 2-methoxycinnamic acid, cis-2-methoxycinnamic acid, 3-methoxycinnamic acid, 4-methylcinnamic acid, 4-methoxycinnamic acid, 2,5-dimethoxycinnamic acid, 3,4-(methylenedioxy)cinnamic acid, 2,4,5-trimethoxycinnamic acid, 3-methylindene-2-carboxylic acid, and trans-3-(4-methylbenzoyl)acrylic acid.

Reaction products of the cured inventive compositions are capable of softening under exposure to elevated temperature conditions, such as an excess of the temperature chosen to cure the composition. Loss of adhesion to the substrate occurs at temperatures greater than that which was used to cure the composition. For instance, at least about 50 percent of adhesion to the substrate is typically lost at temperatures in excess of about 200° C. Furthermore, the reaction products of the compositions of the present invention decompose in dilute acid which provides an additional reworkable aspect.

The epoxide-based curable compounds include cycloaliphatic epoxy, as well as aliphatic epoxy compounds. An example of a useful cycloaliphatic epoxide moiety is one having the following formula:

The reworkable epoxy compositions provided by the present invention may optionally further contain one or more inorganic filler components. The inorganic filler component may include reinforcing silicas, such fused silicas, and may be untreated or treated so as to alter the chemical nature of their surface. Particularly desirable ones have a low ion concentration and are relatively small in particle size (e.g., in the range of about 2–10 microns, such as on the order of about 2 microns), such as the silica commercially available from Admatechs, Japan under the trade designation SO-E5. Other desirable materials for use as the inorganic filler component include those constructed of or containing aluminum oxide, silicon nitride, aluminum nitride, silica-coated aluminum nitride, boron nitride and combinations thereof.

The curing agent components include materials capable of catalyzing the polymerization of the epoxy resin component of the inventive compositions. Desirable curing agents for use with the present invention include nitrogen-containing compounds, such as amines, functionalized amides, and heterocyclic amines, such as imidazoles.

Desirable amines useful as curing agents for the present compositions include diethylenetriamine, triethylenetetramine, diethylaminopropylamine, m-xylenediamine, diaminodiphenylamine, isophoronediamine, menthenediamine, polyamides, melamine-formaldehyde resins, urea-formaldehyde resins, polycarboxylic acid hydrazides, amino phenols, Mannich bases, and combinations thereof.

In another embodiment, the curing agent is a functionalized amide. One suitable example is dicyandiamide.

Useful heterocyclic amines for use as curing agents include, without limitation, the following imidazole compounds: imidazole, isoimidazole, 2-methyl imidazole, 2-ethyl-4-methylimidazole, 2,4-dimethylimidazole, butylimidazole, 2-heptadecenyl-4-methylimidazole, 2-undecenylimidazole, 1-vinyl-2-methylimidazole, 2-n-heptadecylimidazole, 2-undecylimidazole, 2-heptadecylimidazole, 1-benzyl-2-methylimidazole, 1-propyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-guanaminoethyl-2-methylimidazole, addition products of an imidazole and trimellitic acid, addition products of an imidazole and 2-n-heptadecyl-4-methylimidazole, phenylimidazole, benzylimidazole, 2-methyl-4,5-dephenylimidazole, 2,3,5-triphenylimidazole, 2-styrylimidazole, 1-(dodecyl benzyl)-2-methylimidazole, 2-(2-hydroxyl4-t-butylphenyl)4,5-diphenylimidazole, 2-(2-methoxyphenyl)-4,5-diphenylimidazole, 2-(3-hydroxyphenyl)4-,5-diphenylimidazole, 2-(2-hydroxyphenyl)-4,5-diphenylimidazole, di(4,5-diphenyl-2-imidazole)-benzene-1,4, 2-naphthyl-4,5-diphenylimidazole, 1-benzyl-2methylimidazole, 2-p-methoxystyrylimidazole, and combinations thereof.

Primary and secondary amine curing agents are coreactive with the epoxide group. They act as comomomers with the epoxide and are incorporated into the network polymer by a step-growth mechanism. Primary and secondary amine curing agents are typically used in an amount of from about 0.5 to about 2.0 equivalents of amine per equivalent of epoxide. Desirably, primary and secondary amine curing agents are used in an amount of about 1 equivalent of amine per equivalent of epoxide, i.e. two moles of epoxide per mole of primary amine and one mole epoxide per mole of secondary amine. Primary amines are generally desired over secondary amines, although blends may also be employed.

In contrast, tertiary amines, imidazoles, amine-boron trihalide complexes, quaternary ammonium salts, and related curing agents are generally employed as catalysts or initiators of epoxide polymerization. The mechanism is essentially that of an addition homopolymerization reaction and the structure of the cured product is that of a crosslinked polyether. Generally only small amounts of such materials arc used (typically 0.01–10% by weight of epoxy) and the amine may be incorporated into the polymer network at the chain ends. Quaternary phosphonium salts may also be useful as curing agents which are generally employed as catalysts or initiators of epoxide polymerization.

The curing agent bis-(para-aminocyclohexyl)methane is a particularly desirable nitrogen-containing curing agent useful in the present invention.

In another embodiment, the curing agent may be an anhydride. Useful anhydrides include, but are not limited to the following: methyl nadic anhydride, hexahydrophthalic anhydride, trimellitic anhydride, dodecenylsuccinic anhydride, phthalic anhydride, methyl hexahydrophthalic anhydride, tetrahydrophthalic anhydride, methyl tetrahydrophthalic anhydride, 5-(2,5-dioxotetrahydro)3-methyl-3-cyclohexene-1,2-dicarboxylic anhydride, nadic anhydride, maleic anhydride, chloroendic anhydride, pyromellitic dianhydride, succinic anhydride, 3,3'4,4'-benzophenonetetracarboxylic dianhydride, and tetrachlorophthalic anhydride.

In yet another embodiment, the curing agent is a thiol-containing compound. Suitable thiol-containing curing agents include the following: pentaerythritol tetrakis(3-mercaptopropionate); pentaerythritol tetrakis(2-mercaptoacetateate); trimethylolpropane tris(3-mercaptopropionate); trimethylolpropane tris(2-mercaptoacetateate); 1,6-hexanedithol; thiol termianted polysulfides such as Thioplast resins (supplied by Akcros Chemicals); trimercaptan Capcure 3-800 (supplied by Henkel Corp.).

Suitable polyphenols for use as the curing agent in the inventive compositions include: phenol formaldehyde resins (novolac resins and resole resins); 4,4-isoproylidenediphenol (bisphenol A); bis(4-hydroxyphenyl) methane (bisphenol F); poly(4-hydroxyphenol); 4,4'-biphenol; 2,2'-biphenol; pyrogallol, phloroglucinol; 2,3,4'-trihydroxybenzophenone; 1,1,1-tris(4-hydroxyphenyl) ethane; tetrakis(4-hydroxyphenyl)ethane; 2,6-dihydroxynaphthalene; 2,2'-diallylbisphenol A; 1,5-diallyl-2,6-dihydroxynaphthalene; phenol terminated poly(2,6dimethyl-1,4-phenylene ether).

Moreover, the curing agent may be a polyisocyanate. Some examples of useful polyisocyanates are the following: phenyl diisocyanate; toluene diisocyanate (TDI); 4,4-diphenyldiisocyanate; bis(4-isocyanatophenyl)methane; 1,6-hexamethylene diisocyanate (HDI); 1,5-naphthalenediisocyanate; 4,4'-diphenylether diisocyanate; bis(4-isocyanatocyclohexyl)methane; isophorone diisocyanate; tetramethyl-meta-xylidene diisocyanate; 2,2,5-trimethylhexane diissocyanate; HDI-biuret; HDI-isocyanurate; TDI capped poly(ethylene oxide); TDI capped poly(tetramethylene oxide).

Further components may be added to provide the physical properties and characteristics for the compositions and reaction products to render the compositions attractive for commercial use, particularly the micro-electronics industry. For example, the composition may further include a flowability agent, such as a silane and/or titanate. Appropriate silanes for use herein include octyl trimethoxy silane, (commercially available from OSI Specialties Company, Danbury, Conn. under the trade designation A-137), and methacryloxy propyl trimethoxy silane (commercially available from OSI under the trade designation A-174).

Appropriate titanates f6r use as flowabililty agents include titanium for tetrakis [2,2-bis[(2-propepnyloxy)methyl]-1-butanolato-0], [bis(ditridecylphosphito-0)-dihydrogen]₂ (commercially available from Kenrich Petrochemical, Inc., Bayonne, N.J. under the trade designation KR-55). Combinations of these compounds may also be useful. Desirably the flowability agent is used in an amount up to about 2 parts by weight per 100 parts by weight of the epoxy resin compounds. In one embodiment, the composition of the present invention has a viscosity in the range of about 500–100,000 cps.

The composition of the present invention may further include adhesion promoters, such as the silanes, glycidyl trimethoxysilane (commercially available from OSI under the trade designation A-187) or gamma-amino propyl triethoxysilane (commercially available from OSI under the trade designation A-1100).

Cyanate esters may also be used in the inventive compositions. Useful cyanate esters include dicyanatobenzenes, tricyanatobenzenes, dicyanatonaphthalenes, tricyanatonaphthalenes, dicyanatobiphenyl, bis (cyanatophenyl)methanes and alkyl derivatives thereof, bis (dihalocyanatophenyl)propanes, bis(cyanatophenyl)ethers, bis(cyanatophenyl)sulfides, bis(cyanatophenyl)propanes, tris(cyanatophenyl)phosphites, tris(cyanatophenyl) phosphates, bis(halocyanatophenyl)methanes, cyanated novolac, bis[cyanatophenyl(methylethylidene)]benzene, cyanated bisphenol-terminated thermoplastic oligomers, and combinations thereof.

In one particular useful embodiment, the reworkable epoxy resin compositions of the present invention include (a) a curable epoxy component which is the epoxidized reaction product of a multifunctional 1-alkenyl ether, 1-cycloalkenyl ether and a mono-alkenyl carboxylic acid, the epoxy component being present in an amount within the range of about 20 to about 65 weight percent, based on the total weight of the composition; (b) an anhydride curing agent in an amount within the range of about 0.5 to about 1.3 equivalents of anhydride per equivalent of epoxide; (c) optionally, an inorganic filler component in an amount of about 0 weight percent to about 70 weight percent, based on the total weight of the composition; and (d) optionally a flowability agent in an amount of about 0 weight percent to about 0.5 weight percent, based on the total weight of the composition. Desirably, the alkenyl carboxylic acid is a mono-alkenyl carboxylic acid. The anhydride is desirably present at 0.7 to about 0.9 equivalents of anhydride per equivalent of epoxide. In an alternative embodiment, the composition includes as the curing agent a primary or secondary amine curing agent for the epoxy component in an amount within the range of about 0.5 to about 2.0 equivalents of amine per equivalent of epoxide.

The curable epoxy compounds of the present invention may be represented by one of the following formulae:

Formula (a)

Formula (b)

wherein G denotes an organic group derived from a multifunctional 1-alkenyl ether; R represents a $C_1$–$C_6$ alkyl group; E represents an organic group fragment derived from a mono-alkenyl carboxylic acid that has been epoxidized at the alkenyl group; n represents an integer from 2–30; Y denotes an organic group fragment derived from a multifunctional 1-cycloalkenyl ether in which the cyclic ether groups are linked through Y; and m represents the integer 1 or 2. In particular, G may be a hydrocarbon, ether, thioether, ester, thioester, carbamate, amide, or a combination of these groups; G may be a low molar mass entity or an oligomeric or polymeric species. Y in Formula (b) may be attached to the ring portion of the structure at any carbon position other than the carbon atom located between the two oxygen atoms of the acetal fragment or the carbon atom alpha to this position. More specifically, Y may be a hydrocarbon, ether, thioether, ester, thioester carbamate, amide or a combination of these groups; it may be a low molar mass entity or an oligomeric or polymeric species.

In one desired embodiment of the invention, the curable epoxy component is bis-1-(1',6'-hexoxy)ethyl-3,4-epoxycyclohexane carboxylate (BHEC), represented by Formula 2 in Example 1.

Another suitable curable epoxy component for the reworkable epoxy compositions of the invention is bis-3,4- epoxycyclohexane carboxylate of 1,4-cyclohexane dimethanol divinyl ether (ECCD), represented by Formula 3 in Example 2.

A further suitable curable epoxy component of the reworkable epoxy compositions of this invention is tris-3, 4-epoxycyclohexane carboxylate of trimethylolpropane trivinyl ether (ECCT), represented by Formula 4 in Example 3.

As described above, the reaction products of the compositions of the present invention are capable of decomposing under exposure to elevated temperature conditions, which are generally in excess of a temperature chosen to cure the composition. This allows a loss of adhesion to the substrate to occur at temperatures greater than that which was used to cure the composition.

We refer now to Example 5, which shows thermal analysis of cured epoxy compositions of the present invention. In particular, when the curable epoxy component was bis-1-(1',6'-hexoxy)ethyl-3,4-epoxycyclohexane carboxylate (BHEC), and the curing agent for the epoxy component was the anhydride methyl nadic anhydride (MNA) and the catalyst, 2-ethyl-4-methylimidazole (EMI), the composition (Formula A) had an onset temperature of decomposition ($T_d$) of about 227° C. Furthermore, a reworkable epoxy composition of the invention containing a curable epoxy component which was bis-3,4-epoxycyclohexane carboxylate of 1,4-cyclohexane dimethanol divinyl ether (ECCD), and cured by the anhydride MNA and the catalyst EMI (Formulation B) had an onset temperature of decomposition of about 209° C.

Example 5 further shows that a reworkable epoxy composition according to the present invention that included a curable epoxy component which was tris-3,4-epoxycyclohexane carboxylate of trimethylolpropane trivinyl ether (ECCT) and cured by MNA and EMI (Formulation C) had an onset temperature of decomposition of about 196° C. Each of the inventive compositions (A–C) degraded of significantly lower temperatures as compared to a similarly prepared composition containing a commercially available cycloaliphatic epoxide monomer (Formulation D), the onset temperature of degradation for which was 339° C. It is noted that the epoxy monomers included in Formulations A, B and C, have alpha-alkoxy ester groups linking the epoxide functions, whereas the epoxy monomer of the comparative example (Formulation D) has a conventional ester linking group that is not alpha-alkoxy substituted.

Similar results were obtained with amine-cured epoxy compositions according to the present invention. We will refer now to Example 7, which shows thermal analysis of amine-cured epoxy compositions. In particular, when the curable epoxy component was the triepoxide monomer ECCT, described above and in Example 3, and the curing agent was the diamine, bis(para-aminocyclohexyl) methane (PACM) and the catalyst EMI, the composition (Formulation E) had an onset temperature of decomposition ($T_d$) of about 217° C. This inventive composition degraded a temperature significantly lower as compared to the $T_d$ obtained from a similarly prepared composition containing a commercially available cycloaliphatic epoxide monomer (Formulation F), the Td for which was 285° C.

In general, the reworkable epoxy compositions of this invention have decomposition temperatures significantly lower than those of cured formulations of commercially available epoxy monomers, such as diglycidyl ethers of bisphenol A or F, glycidyl ethers of phenol formaldehyde resins, and glycidyl ethers of polyols. For example, the decomposition temperature of a cured formulation of a commercial epoxidized diglycidyl ether of bisphenol F, cured with bis-(para-aminocyclohexyl)methane, is approximately 370° C. For that reason, the curable epoxy component of the reworkable epoxy compositions of this invention have been found to be useful as additives for lowering the decomposition temperature of cured formulations of commercially available epoxy monomers. In particular, the additive of the present invention is a curable epoxy component which is the epoxidized reaction product of multifunctional 1-alkenyl or 1-cycloalkenyl ether and an alkenyl carboxylic acid, the epoxidized reaction product having two or more thermally labile alpha-alkoxy ester linkages and forming a thermally reworkable networked polymer in the presence of a curing agent. The additive is desirably substantially free of unreacted acid or acid impurities. The additive may be represented by Formulae (a) or (b) previously set forth.

In one desirable embodiment of the present invention, there is provided a curable epoxy composition which includes as an additive to a conventional commercially available epoxy monomer composition, one or more of the diepoxide or triepoxide compounds selected from the following: bis-1-(1',6'-hexoxy)ethyl-3,4-epoxycyclohexane carboxylate (BHEC), bis-3,4-epoxycyclohexane carboxylate of 1,4-cyclohexane dimethanol divinyl ether (ECCD); tris-3,4-epoxycyclohexane carboxylate of trimethylolpropane trivinyl ether (ECCT) and combinations thereof. These additives lower the thermal decomposition temperature of conventional, commercially available epoxy monomer compositions, such as those which include a diglycidyl ether of bisphenol F, a glycidyl ether of a polyol or a glycidyl ether of a formaldehyde resin.

The present invention further provides for a method of lowering the decomposition temperature of a cured formulation of a commercially available epoxy resin monomer, wherein the method includes admixing: (a) a curable epoxy component of the present invention which is the epoxidized reaction product of multifunctional 1-alkenyl or 1-cycloalkenyl ether and an alkenyl carboxylic acid (desirably a mono-alkenyl carboxylic acid), wherein the epoxidized reaction product is substantially free of unreacted acid or acid impurities; (b) a commercially available epoxy monomer which desirably includes an epoxidized diglycidyl ether of a bisphenol such as bisphenol F; and (c) a curing agent for the epoxy components, wherein the curing agent is desirably an amine or heterocyclic amine compound or an anhydride compound, and wherein the resultant epoxy composition is thermally decomposable. This method may further include the step of admixing an inorganic filler component into the composition.

The present invention further provides for a method for preparing a reworkable epoxy composition, which when cured provides a composition which is thermally decomposable, said method including admixing: (a) a curable epoxy component which is the epoxidized reaction product of a multifunctional 1-alkenyl or 1-cycloalkenyl ether and an alkenyl carboxylic acid and (b) a curing agent for the epoxy component. Desirably, the reaction product is substantially free of unreacted acid or acid impurities. Suitable curing agents are the same as those described above. This method may further include admixing an inorganic filler component into the composition.

The present invention also provides for a method for synthesizing an epoxy monomer substantially free of unreacted acid and/or acid impurities is herein disclosed. This method includes (a) reacting a 1-alkenyl or 1-cycloalkenyl ether with an alkenyl carboxylic acid (desirably a mono-alkenyl carboxylic acid) at a ratio of at least 1 equivalent of n-functional 1-alkenyl or 1-cycloalkenyl per n equivalents of alkenyl carboxylic acid, where n is an integer within the range 1–6, to form an intermediate; and (b) epoxidizing the carbon-carbon double bonds the intermediate formed in (a) by using a peroxidic reagent. The steps are preformed in the absence of acidic catalysts. Acid catalysts are undesirable as they tend to reduce the storage stability of the epoxide monomer and reduce the degradation temperature of the cured adhesive polymer.

The reaction intermediate formed in step (a) of the synthesis method may be represented by one of the following formulas:

Formula (c)

Formula (d)

wherein G denotes an organic group derived from a multifunctional 1-alkenyl ether; R represents a $C_1$–$C_6$ alkyl group; $R_8$ represents an organic group that contains an alkenyl group; n represents an integer from 2–30; Y denotes an organic group fragment derived from a multifunctional 1-cycloalkenyl ether in which the cyclic ether groups are linked through Y; and m represents the integer 1 or 2.

Reaction conditions may vary depending on the epoxy monomer which is to be formed. However, typically the reaction is performed at a temperature of about 80 to about 100° C. for about 2 to about 50 hours in the absence of an acid catalyst. In one embodiment of the invention, the epoxy monomer is bis-1-(1',6'-hexoxy)ethyl-3,4-epoxycyclohexane carboxylate (BHEC). This monomer is formed by epoxidation of the carbon-carbon double bonds of the intermediate formed from the reaction of the multifunctional vinyl ether, 1,6-hexanediol divinylether and the mono-alkenyl carboxylic acid, 3-cyclohexene-1-carboxylic acid as described in Example 1.

The reactants necessary for formation of the reaction intermediate of the present invention are either commercially available or can be readily synthesized from commercially available raw materials.

In another embodiment of the inventive method, the epoxy monomer is bis-3,4-epoxycyclohexane carboxylate of 1,4-cyclohexane dimethanol divinyl ether (ECCD), which can be prepared by epoxidation of the reaction intermediate formed from the reaction of the multifunctional vinyl ether 1,4-cyclohexane dimethanol divinyl ether with the mono-alkenyl carboxylic acid, 3-cyclohexene-1-carboxylic acid as described in Example 2.

The epoxy monomer formed from the present method can also be tris-3,4-epoxycyclohexane carboxylate of trimethylolpropane trivinyl ether (ECCT), which is prepared by epoxidation of the intermediate formed from the reaction of the multifunctional vinyl ether, trimethylolpropane trivinylether with the mono-alkenyl carboxylic acid, 3-cyclohexene-1-carboxylic acid as described in Example 3.

The present invention further includes a method of assembling an electronic component which includes the step of applying the reworkable epoxy composition of the present invention to a surface of an electronic component. To that end, an electronic device is also provided by this invention wherein the device includes a semiconductor device and a circuit board to which the semi-conductor device is electrically connected, the device itself being assembled using a reworkable epoxy composition according to the present invention.

The reworkable epoxy compositions of the present invention may be of the 1-pack type, in which all the ingredients are mixed together, or of the 2-pack type in which the curable component(s), is (are) included in one part and the curing agent is stored separately in a second part, and mixed together only prior to use.

During application, the reworkable epoxy compositions according to the present invention penetrate and flow readily into the space between the semi-conductor chip and the circuit board, or at least show a reduction in viscosity under heated or use conditions thus penetrating and flowing easily.

Generally, it is desirable to prepare the reworkable epoxy resin compositions of this invention by selecting the types and proportions of various components to reach a viscosity at a temperature of 25° C. in the range of 500 to 100,000 cps, depending on the amount present (if any) of an inorganic filler component,: so as to improve its ability to penetrate into the space (e.g., of 10 to 200 $\mu$m) between the circuit board and a semi-conductor device. At this viscosity, the gel times of the compositions will also be tailored to a specified period of time (such as 15 seconds, or 1 or 2 minutes) at a temperature of about 150° C. With such a gel time, the compositions penetrate into the space between the circuit board and the semi-conductor device relatively rapidly, and allow for a greater number of assemblies to be filled without observing a viscosity increase in the composition thereby rendering it less effective for application.

Using a suitable application means, such as a dispenser, a thermosetting resin composition in accordance with this invention can be applied to the periphery of an electronically-connected semi-conductor chip. The composition penetrates by capillary action into the space between the carrier substrate, i.e. circuit board, and the semi-conductor chip. The thermosetting resin composition is then thermally cured by the application of heat.

Reworkable epoxy compositions of the present invention may ordinarily be cured by heating to a temperature in the range of about 120 to about 180° C. for a period of time of about 0.5 to 30 minutes. However, generally after application of the composition, initial cure time of about 1 minute sets up the composition, and complete cure is observed after about 5 to about 15 minutes at 165° C. Thus the composition of the present invention can be used at relatively moderate temperatures and short-time curing condition, and hence achieve very good productivity.

The amount of the reworkable epoxy composition applied should be suitably adjusted so as to fill almost completely the space between the carrier substrate and a semi-conductor chip, which amount, of course, may vary depending on application.

Cured reaction products of the reworkable epoxy compositions of the present invention demonstrate excellent adhesive force, heat resistance and electric properties, and acceptable mechanical properties, such as flex-cracking resistance, chemical resistance, moisture resistance and the like, for the applications for which they are used herein.

In the mounting process, by using the reworkable epoxy composition of the present invention, after the semi-conductor device is mounted on the circuit board, the resulting structure is tested with respect to characteristics of the semi-conductor device, connection between the semi-conductor device and the circuit board, other electrical characteristics, and the state of sealing. In the event a failure is found, repair can be made in the manner detailed below.

The area around the semi-conductor device which has failed is heated at a temperature of about 190 to about 260° C. for a period of time ranging from about 10 seconds to about 1 minute. Desirably, the temperature should be maintained in the range of about 210 to about 230° C. and the period of time should be within the 30 seconds to 1 minute range. Although no particular limitation is placed on the way in which heating occurs, localized heating is particularly desirable, such as the application of hot air to the failure site by a heating gun.

As soon as the resin is softened by partial decomposition to cause a reduction in bond strength, the semi-conductor device may be pulled apart and removed from the carrier substrate, such as with tweezers or pliers. Any residue remaining from the cured product of the reworkable epoxy compositions can be removed, for example by scraping it off after the residue has been softened by heating it to a predetermined temperature.

Alternatively, the epoxide formulations can be dissolved by hydrolysis of one or more cleavable links. The cleavable links are generally cleaved in aqueous acid, but in order to dissolve the network fragments, an organic solvent may also be necessary. Solvent mixtures containing an alcohol and organic acid are suitable for reworking the cured resin. Useful organic acids include, but are not limited to, methanesulfonic acid and p-tolulenesulfonic acid.

The present invention will be more readily appreciated with reference to the examples which follow.

EXAMPLES

Example 1

Synthesis of bis-1-(1',6'-hexoxy)ethyl-3,4-epoxycyclohexane carboxylate (2) (BHEC)

This example describes a method for preparing a curable epoxy monomer according to the present invention from commercially available reagents. The reaction scheme (Scheme 1) is illustrated below and employs a divinyl ether and a mono-alkenyl carboxylic acid.

1,6-Hexanediol divinylether (17.0 g; 0.05 moles) was added to a 50 mL reaction flask fitted with a thermocouple, magnetic stirrer, addition funnel and heating mantle. The monomer was heated to 75° C. and 3-cyclohexene-1-carboxylic acid (25.2 g; 0.1 moles) was added dropwise over 25 minutes while the temperature was maintained between 75–78° C. After the addition was complete, the stirred mixture was heated for an additional 5 hours and cooled. The crude liquid was vacuum filtered through a short column of basic aluminum to give the intermediate product bis-1-(1', 6'-hexoxy)ethyl cyclohex-3-enecarboxylate (1) (31.96 g; 76% yield). The structure of the product was confirmed by $^1$H NMR and IR spectral analysis.

The intermediate product (1) (8.44 g; 0.02 moles) was dissolved in dichloromethane (30 mL) and the resultant solution added dropwise over 45 minutes to a stirred solution of 3-chloroperoxybenzoic acid (10.62 g of 65% pure grade; 0.04 moles) in dichloromethane (50 mL). The addition was performed in a 250-mL reactor fitted with a thermocouple, addition funnel, magnetic stirrer and ice bath.

The temperature was maintained between 2 and 7° C. throughout the addition. The mixture was stirred for a further 20 hours during which time the temperature was, allowed to slowly increase to the ambient value. The reaction mixture was filtered to remove solids, which were rinsed with dichloromethane (20 mL) and the combined filtrate and rinsings washed with 10% sodium sulfite solution (2×50 mL portions), saturated sodium bicarbonate solution (3×50 mL portions) and deionized water (3×50 mL portions). The washed solution was dried over anhydrous sodium sulfate, filtered and the solvent removed under reduced pressure to yield of BHEC monomer (2) (7.76 g; 86% yield). The structure of the product was confirmed by $^1$H NMR and IR spectral analysis The reaction may be conducted in the absence of an acidic catalyst.

Example 2

Synthesis of bis-3,4epoxycyclohexane carboxylate of 1,4cyclohexane dimethanol divinyl ether (ECCD)

ECCD(3)

This example describes a method of preparing a curable epoxy monomer according to the present invention using a divinyl ether and a mono-alkenyl caroboxylic acid as the starting materials. Each were commercially available.

The bis-epoxide monomer ECCD (3) shown above was prepared in a manner analogous to that described in Example 1. Initially a mixture of 1,4-cyclohexane dimethanol divinyl ether (35.00 g; 0.18 moles) and 3-cyclohexene-1-carboxylic acid (45.00 g; 0.36 moles) was heated at 75–100° C. for 3 hours to prepare the intermediate di-unsaturated α-alkoxyester (100% yield). The intermediate was then epoxidized with 3-chloroperoxybenzoic acid at 0–3° C. according to the process described in Example 1. The product was isolated in 91% yield. The structures of the intermediate and final product were confirmed by $^1$H NMR and IR spectral analysis.

Example 3

Synthesis of tris-3,4-epoxycyclohexane carboxylate of trimethylolpropane trivinyl ether (ECCT) (4)

ECCT (4)

This example describes a method used to prepare an inventive epoxy monomer from a commercially available trivinyl ether and a commercially available mono-alkenyl carboxylic acid. A similar reaction scheme to that shown in Example 1 was used to make the epoxy monomer of the present example, i.e. ECCT (4).

Trimethylolpropane trivinylether (35.4 g; 0.167 moles) was added to a 250-mL reaction flask fitted with a thermocouple, magnetic stirrer, addition funnel and heating mantle. The monomer was heated to 70° C. and 3-cyclohexene-1-carboxylic acid (63.0 g; 0.5 moles) was added dropwise at such a rate as to maintain the temperature between 73–75° C. After the addition was complete, the stirred mixture was heated for an additional 7 hours and cooled. The crude product was dissolved in dichloromethane (100 mL) and the solution passed through a short column of basic alumina. The solvent was then removed by distillation under reduced pressure to give the desired tri-unsaturated α-alkoxyester intermediate (83.0 g; 84% yield). The structure of the product was confirmed by $^1$H NMR and IR spectral analysis.

To a 1-L reactor fitted with a thermocouple, addition funnel, magnetic stirrer and ice bath was added 3-chloroperoxybenzoic acid (112.07 g of 65% pure grade; 0.42 moles) and dichloromethane (350 mL). The mixture was stirred to dissolve the acid and cooled to about 1° C. The tri-functional intermediate product (83.0 g; 0.14 moles) was dissolved in dichloromethane (250 mL) and the resultant solution added dropwise to the reaction mixture at such a rate as to maintained the temperature in the range 1–3° C. (about 2 hours). After the addition was complete the mixture was stirred for a further 2 hours at 1–3° C., filtered and the filtrate washed with 10% sodium sulfite solution (2×400 mL), saturated sodium bicarbonate solution (2×400 mL portions) and deionized water (2×500 mL portions). The washed solution was dried over anhydrous sodium sulfate, filtered and the solvent removed under reduced pressure to yield of ECCT monomer (4) (72.0 g; 80% yield) as a viscous oil. The structure of the product was confirmed by $^1$H NMR and IR spectral analysis.

Example 4

Preparation of Anhydride-cured Epoxy Formulations

Adhesive formulations containing the epoxide monomers of Examples 1–3 were prepared by blending each monomer with a stoichiometric deficiency of curing agent, methyl nadic anhydride (MNA), and a small amount of catalyst, 2-ethyl4-methylimidazole (EMI). The formulation components were blended together in a mechanical mixer to form homogeneous blends of the various formulated products (Formulations A–C, Table 1). For comparative purposes a similar formulation containing a commercially available cycloaliphatic epoxide monomer, 3,4-epoxycyclohexylmethyl 3,4-epoxycyclohexanecarboxylate (Cyracure 6110; supplied by Union Carbide Corporation) was also prepared (Formulation D, Table 1). The formulation details are summarized in Table 1. Except for catalyst EMI, all amounts are in equivalents.

TABLE 1

Formulation of epoxy adhesives

| Component | A | B | C | D |
|---|---|---|---|---|
| BHEC (2) | 1 | | | |
| ECCD (3) | | 1 | | |
| ECCT (4) | | | 1 | |
| Cyracure 6110 | | | | 1 |
| MNA | 0.9 | 0.9 | 0.9 | 0.9 |
| EMI (wt. %) | 0.5 | 0.5 | 0.5 | 0.5 |

Thin film coatings (~0.25 mm) of each liquid formulation (A–D) were prepared on glass slides using a drawdown bar. The coated slides were placed in an oven at 140° C. for 2 hours to cure the adhesive. The cured solid adhesive films were removed from the slides with the aid of a sharp blade. Infrared analysis of the films confirmed that all of the anhydride curing agent was consumed during this time. The cured products were all insoluble in organic solvents indicating that the new epoxide monomers may be cured to give products with useful adhesive properties.

Example 5

Thermal Analysis of Anhydride-cured Formulations

Figure 1:
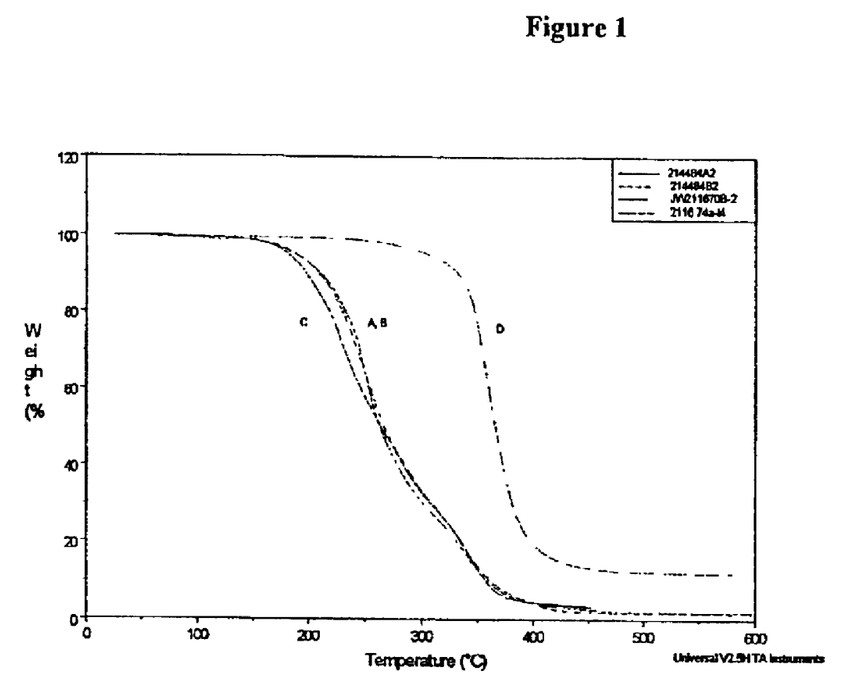
FIG. 1 shows TGA thermograms for anhydride-cured/epoxy resin formulations A–D in Table 1.

Dynamic thermogravimetric analysis (TGA) was carried out on cured formulations A–D which were described in Example 4 at 10° C./min. About 15 mg quantities of each cured composition A–D were placed in separate TGA pans and decomposed on the balance of a thermogravimetric analyzer by heating. The temperature was increased from 90° C. to 600° C. at a heating rate of 10° C./minute and the change in sample weight was recorded as a function of temperature. The onsets of decomposition were determined by step analysis of the weight-loss plot. The results obtained indicated that all of the compositions containing epoxidized alkoxyalkyl esters (A–C) were degraded at significantly lower temperatures as compared to the corresponding conventional epoxy material (D). FIG. 1 shows the TGA traces. The related thermal data is outlined in Table 2 below.

TABLE 2

Results of TGA analysis of cured MNA/AAE epoxy compositions A–D

| Formulation | Onset of Degradation (° C.) | Weight loss at 200° C. (%) |
|---|---|---|
| A | 227 | 7.3 |
| B | 209 | 6.9 |
| C | 196 | 10.9 |
| D | 339 | 0.5 |

These data show that compositions A–C exhibit little or no decomposition at temperatures below 200° C. However, at temperatures in the range 200–250° C., they exhibit rapid decomposition and are, therefore, particularly suitable for use as reworkable adhesives.

Example 6

Preparation of Amine-cured Epoxy Formulations

An adhesive formulation containing the triepoxide monomer of Example 3 was prepared by mixing the monomer with a diamine curing agent, bis(para-aminocyclohexyl) methane (PACM), and a catalyst, 2-ethyl-4-methylimidazole (EMI). The formulation was blended together by hand to form a homogenous blend. For comparative purposes, a control formulation containing Cyracure 6110 was also prepared. The formulation details are summarized in Table 3. A small amount of each was placed on a glass slide and the slide placed in an oven at 140° C. for two hours for curing.

TABLE 3

Formulation of epoxy adhesives

| Component | E | F |
|---|---|---|
| ECCT | 8.0 g | |
| Cyracure 6110 | | 8.0 g |
| PACM | 1.5 g | 1.5 g |
| EMI | 0.4 g | 0.4 g |

Example 7

Thermal Analysis of Amine-cured Formulations

Figure 2:
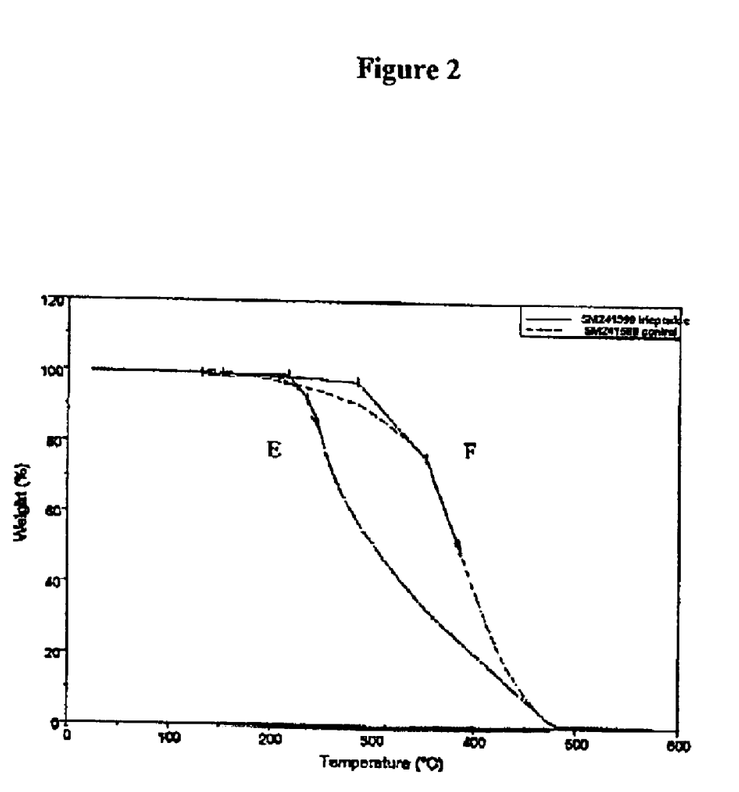
FIG. 2 shows TGA thermograms for amine-cured epoxy formulations E and F in Table 3.

Dynamic thermogravimetric analysis performed on the cured formulations from Example 6 at a heating rate of 10° C./min. The onsets of decomposition were determined by step analysis and showed that the amine-cured triepoxide containing the alkoxyalkyl ester functionality (Formulation E) degraded at a significantly lower temperature than the conventional diepoxide used as a control (Formulation F). FIG. 2 shows the TGA traces. The thermal data is outlined in Table 4.

TABLE 4

TGA analysis of epoxy formulations E and F

| Formulation | Onset of Degradation (° C.) | Weight loss at 250° C. |
|---|---|---|
| E | 217 | 19.3% |
| F | 285 | 5.9% |

What is claimed is:
1. An epoxy composition comprising the epoxidized reaction product of a multifunctional 1-alkenyl or

1-cycloalkenyl ether and an alkenyl carboxylic acid, said epoxidized reaction product having two or more thermally labile alpha-alkoxy ester linkages.

2. The composition of claim 1, wherein the reaction products of the composition, when cured, are capable of softening and losing their adhesiveness under exposure to temperature conditions in excess of those used to cure the composition.

3. The composition of claim 1, wherein said alkenyl carboxylic acid is a mono-alkenyl carboxylic acid.

4. The composition of claim 1, wherein the multifunctional 1-alkenyl ether is selected from the group consisting of 1,6-hexanediol divinylether, 1,4-cyclohexane dimethanol divinyl ether, trimethylolpropane trivinylether, diethyleneglycol divinyl ether, polyoxyethylene divinyl ether, ethyleneglycol divinyl ether, tetraethyleneglycol divinyl ether, bis[4-(vinyloxy)butyl]isophthalate, bis[4-(vinyloxymethyl)cyclohexylmethyl]glutarate, bis[4-(vinyloxy)butyl]succinate, bis[4-(vinyloxy)butyl]adipate, bis[4-(vinyloxy)butyl](methylene di-4,1-phenylene)biscarbamate, tris[4-(vinyloxy)butyl]trimellitate, butanediol divinyl ether, nonandiol divinylether, cyclohexanediol divinylether, pentaerythritol-tetravinyl ether, 1,4-dipropenoxybutane, 1,6-dipropenoxyhexane, 1,6-dipropenoxyoctane, 1,10-dipropenoxydecane, diethyleneglycoldipropenyl ether, neopentylglycoldipropenyl ether, triethyleneglycoldipropenyl ether, trimethylolpropanetripropenyl ether, 1,2,3-tripropenoxypropane, pentaerythritoltetrapropenyl ether, and sorbitolhexapropenyl ether.

5. The composition of claim 1, wherein the alkenyl carboxylic acid is a mono-alkenyl carboxylic acid selected from the group consisting of 3-cyclohexene-1-carboxylic acid, 2-hexenoic acid, 3-hexenoic acid, 4-hexenoic acid, acrylic acid, methacrylic acid, crotonic acid, vinyl acetic acid, tiglic acid, 3,3-dimethylacrylic acid, trans-2-pentenoic acid, 4-pentenoic acid, trans-2-methyl-2-pentenoic acid, 2,2-dimethyl-4-pentenoic acid, trans-2-hexenoic acid, trans-3-hexenoic acid, 2-ethyl-2-hexenoic acid, 6-heptenoic acid, 2-octenoic acid, (+/−)-citronellic acid, (R)-(+)-citronellic acid, (S)-(−)-citronellic acid, undecylenic acid, myristoelic acid, palmitoleic acid, oleic acid, elaidic acid, cis-11-eicosenoic acid, erucic acid, nervonic acid, cis-3-chloroacrylic acid, trans-3-chloroacrylic acid, 2-bromoacrylic acid, 2-(trifluoromethyl)acrylic acid, 2-(bromomethyl)acrylic acid, 2-cyclopentene-1-acetic acid, (1R-trans)-2-(bromomethyl)-2-methyl-3-methylenecyclopentaneacetic acid, 2-acetamidoacrylic acid, 5-norbornene-2-carboxylic acid, 3-(phenylthio)acrylic acid, trans-styrylacetic acid, trans-cinnamic acid, alpha-methylcinnamic acid, alpha-phenylcinnamic acid, 2-(trifluoromethyl)cinnamic acid, 2-chlorocinnamic acid, 2-methoxycinnamic acid, cis-2-methoxycinnamic acid, 3-methoxycinnamic acid, 4-methylcinnamic acid, 4-methoxycinnamic acid, 2,5-dimethoxycinnamic acid, 3,4-(methylenedioxy)cinnamic acid, 2,4,5-trimethoxycinnamic acid, 3-methylindene-2-carboxylic acid, and trans-3-(4-methylbenzoyl)acrylic acid.

6. The composition of claim 1, wherein the epoxidized reaction product is within one of the following formulae:

Formula (a)

Formula (b)

wherein G denotes an organic group derived from a multifunctional 1-alkenyl ether; R represents a $C_1$–$C_6$ alkyl group; E represents an organic group fragment derived from a mono-alkenyl carboxylic acid that has been epoxidized at the alkenyl group; n represents an integer from 2–30; Y denotes an organic group fragment derived from a multifunctional 1-cycloalkenyl ether in which the cyclic ether groups are linked through Y; and m represents the integer 1 or 2.

7. A method for synthesizing an epoxy monomer comprising the steps of (a) reacting a 1-alkenyl or 1-cycloalkenyl ether with an alkenyl carboxylic acid at a ratio of at least 1 equivalent of n-functional 1-alkenyl or 1-cycloalkenyl ether per n equivalents of mono-alkenyl carboxylic acid, where n is an integer within the range of 1–6, to form an intermediate; and (b) epoxidizing the carbon-carbon double bonds of the intermediate formed in step (a).

8. A method of assembling an electronic component comprising applying a reworkable epoxy composition comprising the epoxidized reaction product of a multifunctional 1-alkenyl or 1-cycloalkenyl ether and an alkenyl carboxylic acid to a surface of an electronic component, and permitting said composition to cure.

* * * * *